United States Patent
Jackson et al.

(10) Patent No.: US 8,980,221 B2
(45) Date of Patent: Mar. 17, 2015

(54) FLUORIDE PROCESSING METHOD

(75) Inventors: Alexander Jackson, Little Chalfont (GB); Rajiv Bhalla, Little Chalfont (GB)

(73) Assignee: GE Healthcare Limited, Buckinghamshire (GB)

( * ) Notice: Subject to any disclaimer, the term of this patent is extended or adjusted under 35 U.S.C. 154(b) by 397 days.

(21) Appl. No.: 12/810,893

(22) PCT Filed: Dec. 22, 2008

(86) PCT No.: PCT/EP2008/068155
§ 371 (c)(1),
(2), (4) Date: Jun. 28, 2010

(87) PCT Pub. No.: WO2009/083530
PCT Pub. Date: Jul. 9, 2009

(65) Prior Publication Data
US 2010/0285570 A1    Nov. 11, 2010

Related U.S. Application Data

(60) Provisional application No. 61/018,691, filed on Jan. 3, 2008.

(51) Int. Cl.
A61K 51/00 (2006.01)
A61M 36/14 (2006.01)
C07D 487/08 (2006.01)
C01B 9/08 (2006.01)
C07B 59/00 (2006.01)

(52) U.S. Cl.
CPC ............... C07D 487/08 (2013.01); C01B 9/08 (2013.01); C07B 59/002 (2013.01)
USPC ........................................................ 424/1.89

(58) Field of Classification Search
None
See application file for complete search history.

(56) References Cited

U.S. PATENT DOCUMENTS

| | | | | |
|---|---|---|---|---|
| 4,548,917 | A | * | 10/1985 | Lepage et al. ............... 502/150 |
| 5,425,063 | A | * | 6/1995 | Ferrieri et al. ............... 376/195 |
| 5,728,843 | A | | 3/1998 | Wallace et al. |
| 7,723,322 | B2 | | 5/2010 | Mascal |
| 2007/0232521 | A1 | | 10/2007 | Mascal |

FOREIGN PATENT DOCUMENTS

| | | |
|---|---|---|
| EP | 2008/155339 | 12/2008 |
| WO | 03/002157 | 1/2003 |
| WO | 03/075508 | 4/2003 |
| WO | 2004/041432 | 5/2004 |
| WO | 2005006141 | 7/2005 |
| WO | 2005/097713 | 10/2005 |
| WO | 2006/071470 | 7/2006 |
| WO | 2007/020400 | 2/2007 |

OTHER PUBLICATIONS

Regen (Angew. Chem. Int. Ed. 1979, 18, 421-429).*
Jewett et al. (Appl. Radiat. Isot. 1988, 39, 1109-1111).*
Hamacher et al. (J. Nucl. Med. 1986, 27, 235-238).*
Ilioudis et al. (J. Am. Chem. Soc. 2004, 126, 12395-12402).*
Tomoi et al. (J. Polymer Sci. 1984, 22, 911-926).*
Montanari et al. (J. Org. Chem. 1981, 46, 2125-2130).*
Tomoi "Phase Transfer Reactions Catalyzed by Polymer Supported Crown Ethers" Journal of Polymer Science, vol. 22, 1984 pp. 911-926.
Basallote, et al. "Exploring the Properties and Optical Sensing Capability of Sol-Gel Materials Containing a Covalently Bonded Binucleating Cryptand" Chem Matterl., vol. 15, 2003, pp. 2025-2032.
Reilly, et al. "Octaazacryptand Complexationof the Fluoride Ion" Inorganic Chemistry,, vol. 34, 1995, pp. 569-575.
Mascal, et al. "Fluoride-Selectrive Host Based on Anion-pi Interactions, Ion Pairing, an Dhydrogen Bonding: Synthesis and Fluoride-Ion Sandwich Complex" Angew. Chem. Int. Ed. 2007, vol. 46, pp. 8782-8784.
PCT/EP008068155 ISRWO Dated Aug. 28, 2009.
GB0800029.1 Search Report Dated Apr. 30, 2008.
Snyder, "Introduction to Modern Liquid Chromatograpy" Wiley-Interscience 1979 pp. 423-426.

* cited by examiner

*Primary Examiner* — Michael G Hartley
*Assistant Examiner* — Melissa Perreira

(57) ABSTRACT

The invention relates to methods for processing [$^{18}$F]-fluoride target water using a solid-support bound Cryptand of formula (I) and to apparatus for performing such methods. The resultant [$^{18}$F]-fluoride is useful for preparation of radiopharmaceuticals by nucleophilic fluorination, specifically for use in Positron Emission Tomography (PET).

(I)

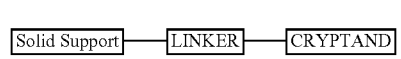

6 Claims, No Drawings

FLUORIDE PROCESSING METHOD

This application is a filing under 35 U.S.C. 371 of international application number PCT/EP2008/068155, filed Dec. 22, 2008, which claims priority to U.S. provisional application No. 61/018,691, filed Jan. 3, 2008, the entire disclosure of which is hereby incorporated by reference.

The present invention relates to methods for processing [$^{18}$F]-fluoride target water, and to apparatus for performing such methods. The resultant [$^{18}$F]-fluoride is useful for preparation of radiopharmaceuticals by nucleophilic fluorination, specifically for use in Positron Emission Tomography (PET).

Fluorine-18 is obtained by a variety of nuclear reactions from both particle accelerators and nuclear reactors, and can be produced at specific activities approaching $1.71 \times 10^9$ Ci/mmol. The half-life of fluorine-18 is 109.7 minutes, relatively long in comparison with other commonly used radioisotopes but still imposing time constraints on processes for preparing $^{18}$F-labelled radiopharmaceuticals.

Most fluorine-18 is produced by irradiation of an [$^{18}$O] oxygen gas target by the nuclear reaction $^{18}$O(p,n)$^{18}$F, and isolated as [$^{18}$F]fluoride ion in aqueous solution. In aqueous form, [$^{18}$F]fluoride can be relatively unreactive, and so certain steps are routinely performed to provide a reactive nucleophilic [$^{18}$F]fluoride reagent.

Following irradiation, a positively charged counterion is added, most commonly potassium complexed by a cryptand such as Kryptofix 222 (4,7,13,16,21,24-hexaoxa-1,10-diazabicyclo[8,8,8]hexacosan), or alternatively, cesium, rubidium, or a tetralkylammonium salt. This is commonly achieved by passing the [$^{18}$F]fluoride target water (typically in volumes of 1 to 5 mL) through an anion exchange resin and eluting with an aqueous organic solution (typically in a volume of 0.3 to 1 mL) of the counterion, for example, with a potassium carbonate/Kryptofix solution in water/acetonitrile. Secondly, the solution is dried, commonly by azeotroping in the presence of a low-boiling solvent such as acetonitrile. Automated radiosynthesis apparatus routinely include such a drying step, typically lasting 9 minutes in the case of [$^{18}$F] FDG synthesis on Tracerlab MX (GE Healthcare). The compound to be labelled (dissolved in an organic solvent suitable for performing the subsequent radiosynthesis, usually an aprotic solvent such as acetonitrile, dimethylsulphoxide or dimethylformamide) is then added to the dried residue of [$^{18}$F]fluoride and counterion.

However, there still exists a need for efficient [$^{18}$F]fluoride processing methodologies which allow rapid, efficient trapping and elution of [$^{18}$F]fluoride from target water. Additionally, there is a need for such methodologies which are amenable to automation to facilitate improved preparation of radiopharmaceuticals in the clinical setting.

Accordingly, the present invention provides a method for preparing an [$^{18}$F]fluoride solution which comprises:

(i) contacting a solution of [$^{18}$F]fluoride in water with a solid-support bound Cryptand of formula (I)

(I)

at a pH of less than 5 so as to form a Cryptand-[$^{18}$F]fluoride complex of formula (II):

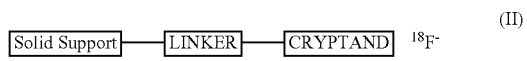

(II)

(ii) removal of excess water from the Cryptand-[$^{18}$F]fluoride complex of formula (II);

(iii) washing the Cryptand-[$^{18}$F]fluoride complex of formula (II) with a solution of base, suitably a base having a pKa of at least 9, so as to release the [$^{18}$F]fluoride into solution.

In formula (I), the Solid Support may be any suitable solid-phase support which is insoluble in any solvents to be used in the method but to which the Linker and/or Cryptand may be covalently bound. Examples of suitable Solid Support include polymers such as polystyrene (which may be block grafted, for example with polyethylene glycol), polyacrylamide, or polypropylene, or glass or silicon coated with such a polymer. The Solid Support may take the form of small discrete particles such as beads or pins, or as coatings on a particle, for example, of glass or silicon, or a coating on the inner surface of a cartridge or microfabricated device.

In formula (I), the Linker is a $C_{1-50}$ hydrocarbyl group optionally further including 1 to 10 heteroatoms such as oxygen or nitrogen. Suitable Linker groups include alkyl, alkenyl, alkynyl chains, aromatic, polyaromatic, and heteroaromatic rings (for example, triazoles), and polymers comprising ethyleneglycol, amino acid, or carbohydrate subunits any of which may be optionally substituted for example with one or more ether, thiooether, sulphonamide, or amide functionality.

The compounds of formula (I) may be pre-conditioned by treatment with an acid solution to form a protonated derivative, or may be non-conditioned.

As used herein, the term "Cryptand" means a bi- or polycyclic multidentate ligand for the fluoride anion. Suitable Cryptands for binding anions such as fluoride have been reviewed in J. W. Steed, J. L. Atwood in Supramolecular Chemistry (Wiley, New York, 2000), pp 198-249; Supramolecular Chemistry of Anions, Eds. A Bianchi, K Bowmann-James, E. Garcia-Espana (Wiley-VCH, New York, 1997), and P. D. Beer, P. A. Gale, Angew. Chem. 2001, 113, 502; Angew. Chem. Int. Ed. 2001, 40, 486.

Suitable Cryptands used herein include those of formula (C):

(C)

wherein:

R1 and R2 are independently selected from

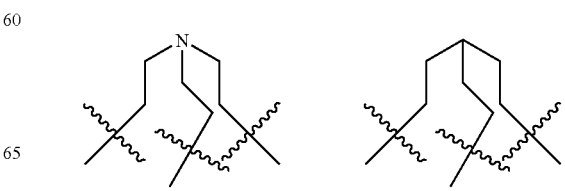

-continued
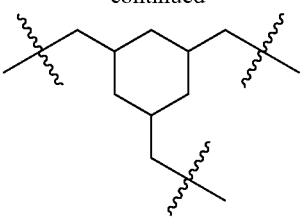
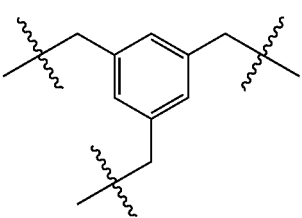
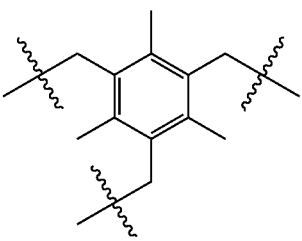
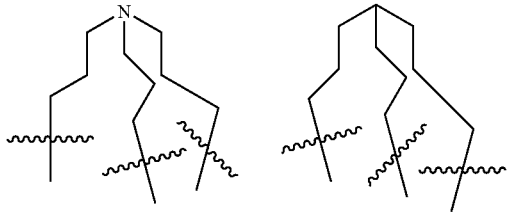
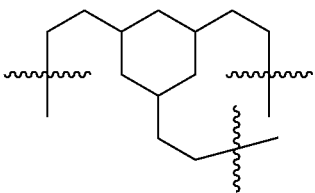
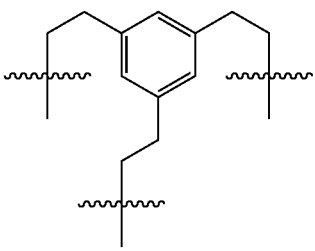
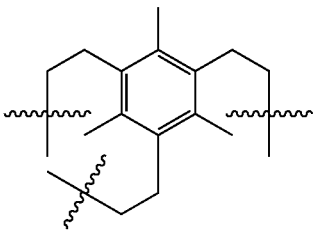
-continued
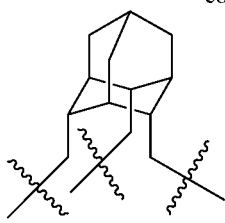 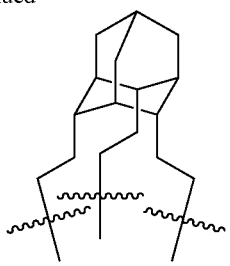
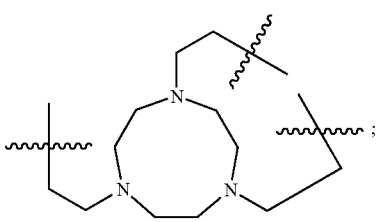
and
R3, R4, and R5 are independently selected from:
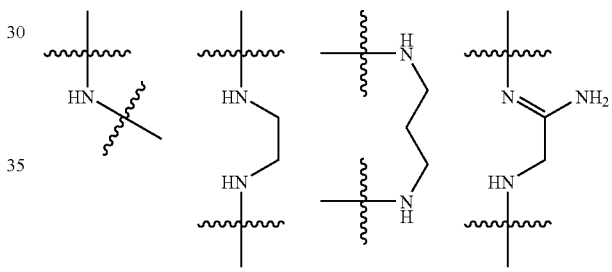
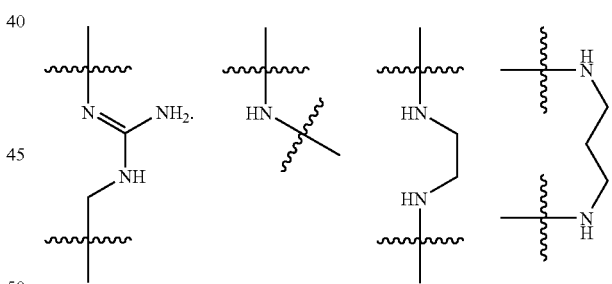
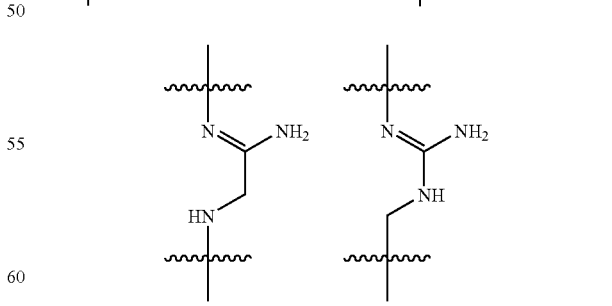
Preferred Cryptands useful in the invention may be selected from:

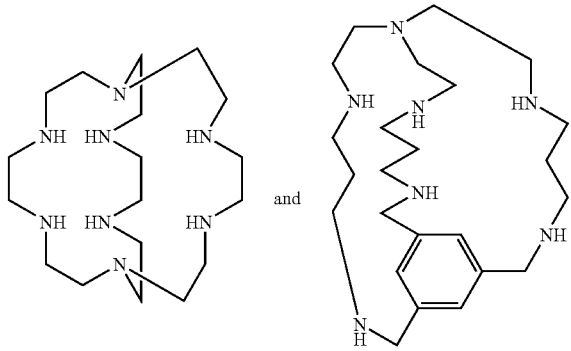 [SMILES: C1CNCCN2CCNCCNCCN(CCN1)CCNCCNCC2 ; "and" ; c1c2cc3cc1CNCCCNCCN(CCNCCCNC2)CCNCCCNC3]

or may be chosen to have desirable properties such as a high binding constant for fluoride, high stability of the fluoride bound complex and high fluoride selectivity over other anions.

In the compounds of formula (I), the Cryptand is attached to a Linker group. The point of attachment may be a nitrogen or carbon atom in the Cryptand. Thus the point of attachment to the Linker "L" may be in group R1 or R2:

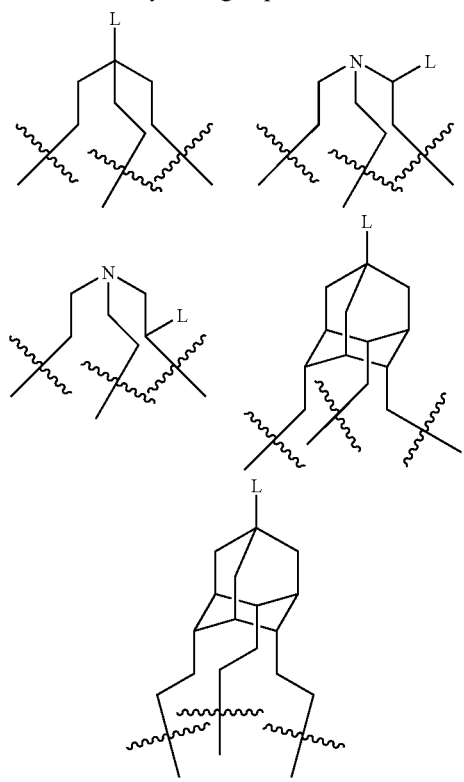

or in R3, R4, or R5:

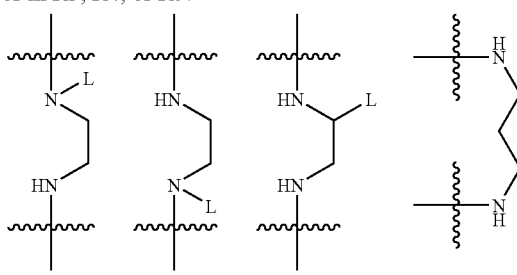

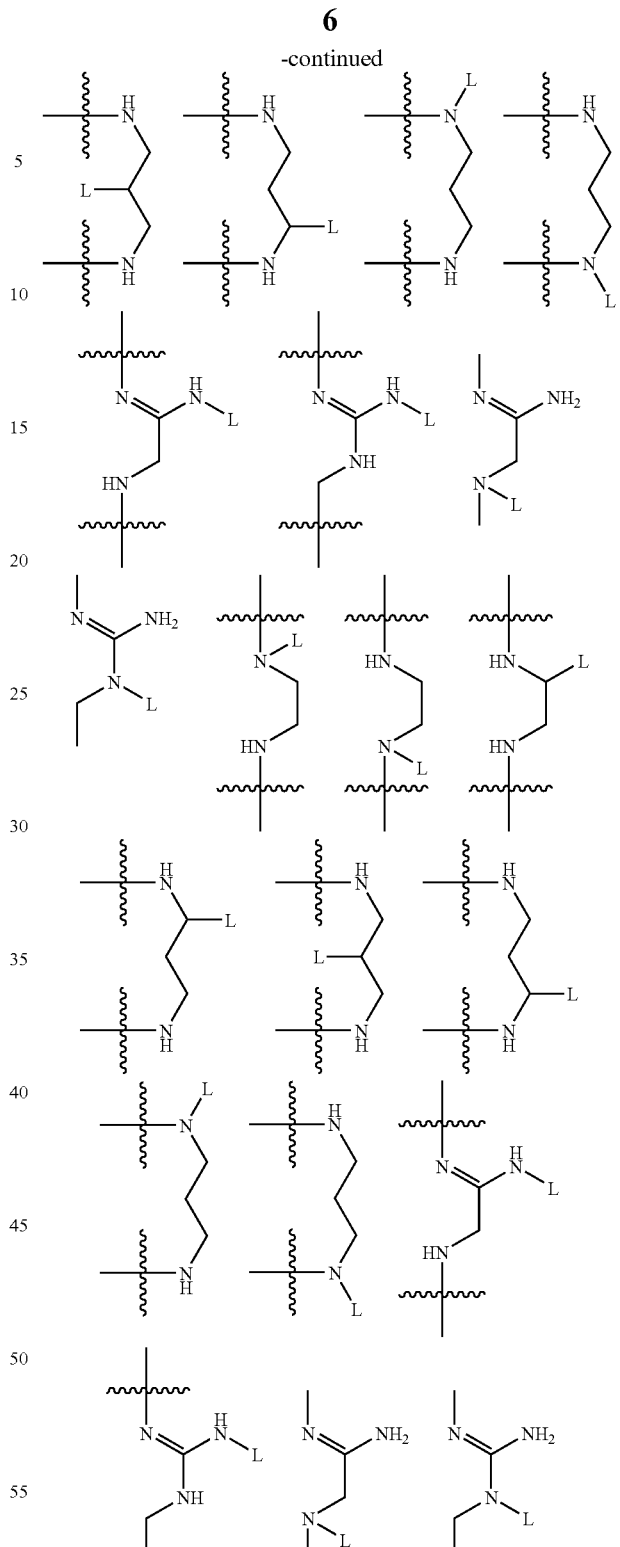

The method of the invention may be performed by contacting the solid-support bound Cryptand of formula (I) with the solution of [$^{18}$F]fluoride in water in a container and then separating the resulting solid-phase Cryptand-[$^{18}$F]fluoride complex of formula (II) by filtration. Alternatively, and particularly suitably when the solid-support bound Cryptand of formula (I) is used within an automated apparatus, the solid-support bound Cryptand of formula (I) may be contained in a vessel either as discrete particles or as a coating through which the solution of [$^{18}$F]fluoride in water is passed. The solution of [$^{18}$F]fluoride in water may be passed through the vessel containing solid-support bound Cryptand of formula (I) as a continuous flow, for example at a flow rate of from 0.1 ml/min to 100 ml/min, or in batches, so as to permit sufficient residence time on the solid-phase for the fluoride complexation to occur. As would be understood by the person skilled in the art, the solid-support bound Cryptand of formula (I) may be held in any suitable vessel such as a plastic or metal column, cartridge, or syringe barrel. The fluoride complexation is conveniently performed at ambient temperature, but use of non-extreme elevated temperature (for example up to 120° C., but preferably up to 80° C.) can increase efficiency of the fluoride complexation.

Step (iii) of the process ie. washing the Cryptand-[$^{18}$F]fluoride complex of formula (II) with a solution of base, suitably a base having a pKa of at least 9, so as to release the [$^{18}$F]fluoride into solution is suitably effected in a similar manner to steps described above, the solid-support facilitating separation of the [$^{18}$F]fluoride in solution. The base is suitably selected from a potassium salt (such as potassium carbonate, potassium bicarbonate, or potassium sulphate) optionally in the presence of a phase transfer catalyst such as Kryptofix; a tetraalkylammonium salt (such as tetraalkylammonium carbonate, tetralkylammonium bicarbonate, or tetraalkylammonium sulphate); a phosphonium salt (such as phosphonium carbonate, phosphonium bicarbonate, or phosphonium sulphate); a cesium salt (such as cesium carbonate, cesium bicarbonate, or cesium sulphate); and an imidazolium salt (such as imidazolium carbonate, imidazolium bicarbonate, or imidazolium sulphate) and is provided in a solution comprising organic solvent (suitably selected from acetonitrile, dimethylformamide, dimethylsulfoxide, tetrahydrofuran, dioxan, 1,2-dimethoxyethane, sulfolane or N-methylpyrrolidinone or a mixture of any thereof), water, or an organic solvent containing water. Suitably, the solution is formed in a dry organic solvent (i.e. containing less than 1000 ppm water), or an organic solvent containing water at a level which is tolerated in the subsequent radiofluoridation reaction, for example 1000 ppm to 50,000 ppm water, preferably 1000 to 15,000 ppm, more preferably 2000 ppm to 7000 ppm, suitably 2500 ppm to 5000 ppm, as is taught in WO 2006/054098. In this way, a further drying step before radiofluoridation may be avoided.

In one aspect of the invention, step (iii) is performed using a small volume of base solution, such as 400 μl or less, preferably 50 μl or less, and more preferably 1 to 10 μl. The [$^{18}$F]fluoride solution is then obtained in highly concentrated form which is advantageous as the volume of water present is correspondingly low which means the customary step of drying the [$^{18}$F]fluoride solution before performing a radiofluoridation reaction can be shorter or avoided altogether. Also, this aspect of the invention makes the method amenable to automation, and particularly in a smaller reaction vessel such as a miniaturised device.

An [$^{18}$F]fluoride solution produced by the method of the invention may then be used in radiosynthetic processes, to perform nucleophilic [$^{18}$F]fluoridation of a Vector.

As used herein, the term "Vector" means a biomolecule suitable for radiolabelling to form a radiopharmaceutical, such as a peptide, protein, hormone, polysaccharide, oligonucleotide, antibody fragment, cell, bacterium, virus, or small drug-like molecule.

The reaction of a Vector with an [$^{18}$F]-fluoride solution produced by the method of the invention may be effected at an elevated temperature, for example up to 200° C. or at non-extreme temperature, such as 10° C. to 50° C., and most preferably at ambient temperature. The temperature and other conditions for radiofluoridation being selected according to the exact reaction being performed, nature of reaction vessel, solvents etc as would be apparent to a person skilled in the art.

Following [$^{18}$F]-fluoridation, a purification step may be required which may comprise, for example, removal of excess [$^{18}$F]-fluoride, removal of solvent, and/or separation from unreacted Vector. Excess [$^{18}$F]-fluoride may be removed by conventional techniques such as ion-exchange chromatography (for example using BIO-RAD AG 1-X8 or Waters QMA) or solid-phase extraction (for example, using alumina). Excess solvents may be removed by conventional techniques such as evaporation at elevated temperature in vacuo or by passing a stream of inert gas (for example, nitrogen or argon) over the solution. Alternatively, the [$^{18}$F]-fluoridated Vector may be trapped on a solid-phase, for example a cartridge of reverse-phase absorbant for example a $C_{5-18}$ derivatized silica, whilst the unwanted excess reagents and by-products are eluted, and then the [$^{18}$F]-fluoridated Vector may be eluted from the solid-phase in purified form.

Selection and synthesis of a Solid Support and/or Linker in a compound of formula (I) may be effected by conventional techniques of solid phase chemistry, for example as described in Florencio Zaragoza Dorwald "Organic Synthesis on Solid Phase; Supports, Linker, Reactions", Wiley-VCH (2000).

Compounds of formula (I) may be prepared by reacting a compound of formula (III):

(III)

with a compound of formula (IV):

(IV)

wherein the Solid Support and Cryptand are as defined above, Linker' is a portion of the Linker as defined above, and $R^{III}$ and $R^{IV}$ are reactive groups capable of covalent bonding to each other so as to complete formation of the Linker. Suitably, one of $R^{III}$ and $R^{IV}$ is an amine and the other is a carboxylic acid or an activated carboxylic ester, isocyanate or isothiocyanate such that the compounds of formulae (III) and (IV) may be joined by simple amide forming reaction. Suitable activated carboxylic esters include the N-hydroxysuccinimidyl and N-hydroxysulfosuccinimidyl esters:

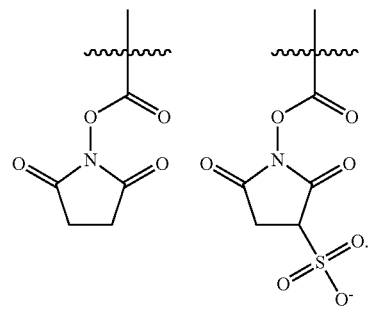 [SMILES: *C(=O)ON1C(=O)CCC1=O ; *C(=O)ON1C(=O)CC(S(=O)(=O)[O-])C1=O]

Alternatively one of $R^{III}$ and $R^{IV}$ may be a thiol and the other a group reactive towards a thiol, such as a maleimide or an α-halocarbonyl.

As would be apparent to the person skilled in the art, it may also be desirable for the Cryptand in the Compound of formula (III) to have protection groups on any exposed functional groups e.g. amino groups to prevent or reduce side-reactions during conversion to a Compound of formula (I). In these cases the protection group will be chosen from those commonly used for the functional group in question e.g tert-butylcarbamate for an amine. Other suitable protecting groups may be found in Protecting Groups in Organic Synthesis, Theodora W. Greene and Peter G. M. Wuts, published by John Wiley & Sons Inc. which further describes methods for incorporating and removing such protecting groups.

Certain compounds of formula (I) may be prepared by reacting a compound of formula (III) wherein $R^{III}$ is either an amino or carboxylic acid group with a compound of formula (IV) wherein $R^{IV}$ is either a carboxylic acid or amine group respectively. In these cases a compound of formula (III) may be coupled with a compound of formula (IV) optionally using in situ activating agents such as 2-(1H-benzotriazole-1-yl)-1,1,3,3-tetramethyluronium hexafluorophosphate (H BTU) or N-[(dimethylamino)-1H-1,2,3-triazolo[4,5-b]pyridin-1-yl-methylene]-N-methylmethanamonium hexafluorophosphate N-oxide (HATU). Standard conditions will be used e.g. dimethylformamide (DMF) solution and a base e.g. triethylamine or diisopropylethylamine. Alternatively where $R^{IV}$ in the compound of formula (IV) is a thiol group, this may be reacted with a compound (III) in which $R^{III}$ is a thiol reactive group such as a maleimide or an α-halocarbonyl. This reaction may be performed in a pH buffered solution or an organic solvent. The product compound having the formula (II) might be purified by preparative high performance liquid chromatography.

The Cryptands may be synthesised as described in US20040267009 A1, Bernard Dietrich, Jean-Marie Lehn, Jean Guilhem and Claudine Pascard, Tetrehedron Letters, 1989, Vol. 30, No. 31, pp 4125-4128, Paul H. Smith et al, J. Org. Chem., 1993, 58, 7939-7941, Jonathan W. Steed et al, 2004, Journal of the American Chemical Society, 126, 12395-12402, Bing-guang Zhang et al, Chem. Comm., 2004, 2206-2207.

The synthesis of a Compound of formula (III) may be achieved as described in the above references for the underivatized Cryptands with modifications to the starting materials or by subsequent chemistry, for example, by alkylation of a secondary amine group of the Cryptand as illustrated in the Examples below. Compounds of formula (III) may also be prepared as shown in Schemes 2 to 5 in which L and R''' are as defined above for the Compound of formula (III).

Scheme 2

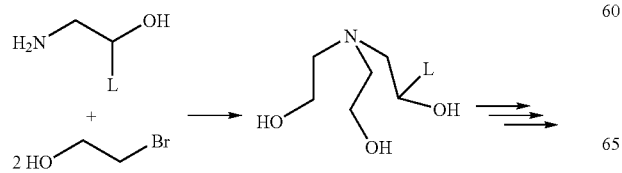

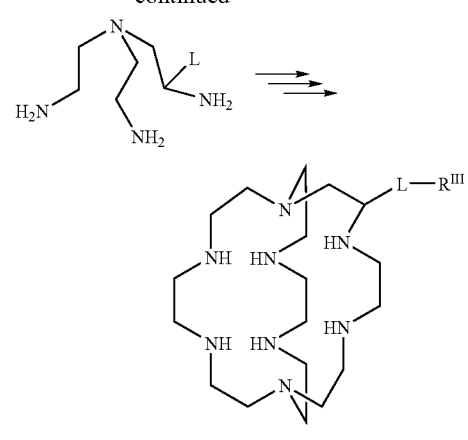

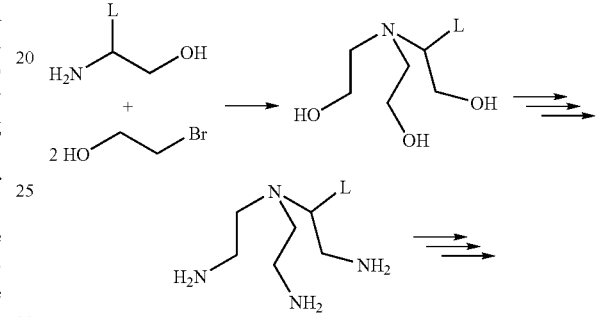

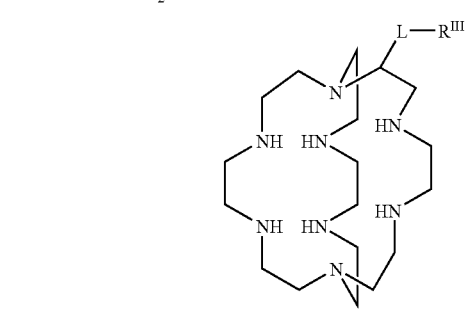

-continued

Scheme 3

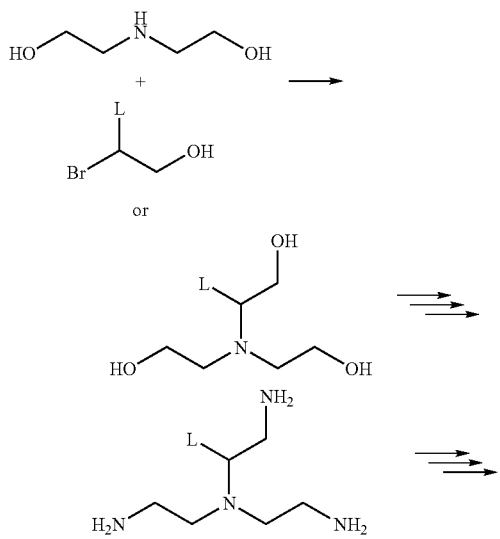

-continued
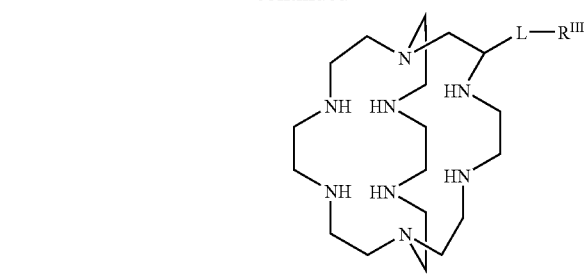
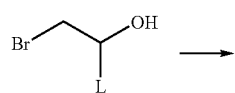
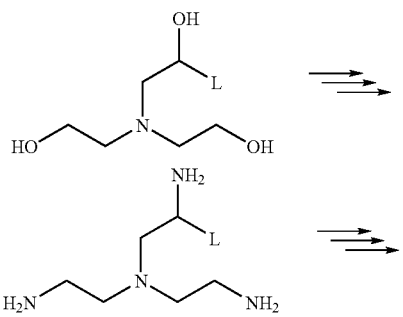
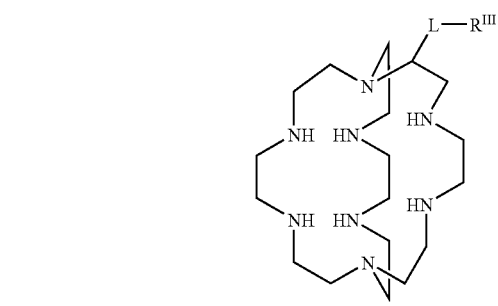
Scheme 4
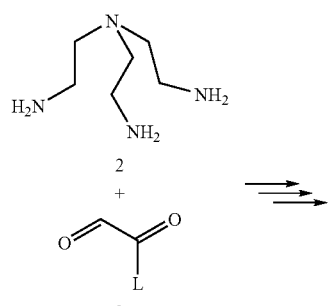
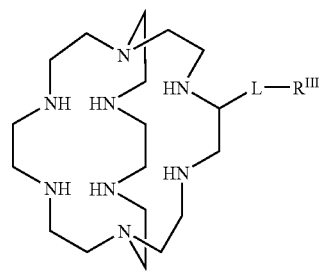
Scheme 5
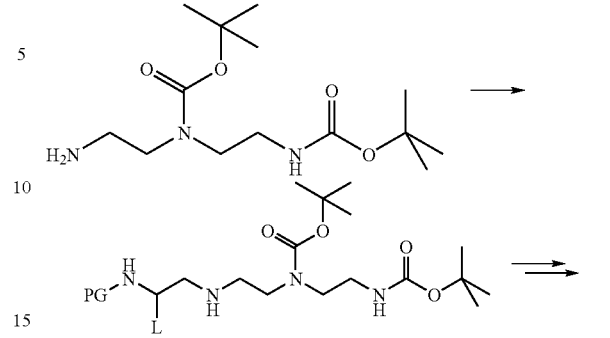
PG = protecting group
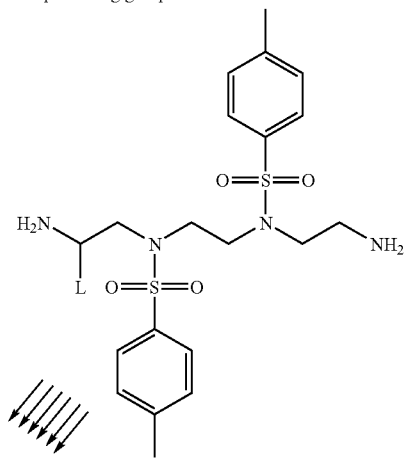
Certain solid-support bound cryptands are novel. Therefore, as a further aspect of the invention, there is provided a compound of formula (I):
wherein the Solid Support and Linker are as defined above, and the Cryptand is of formula (C):
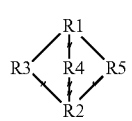

wherein:
R1 and R2 are independently selected from
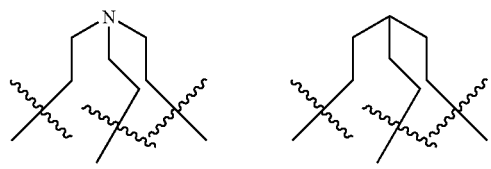
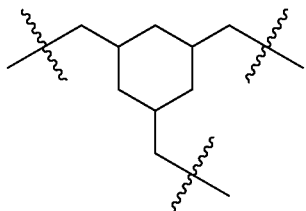
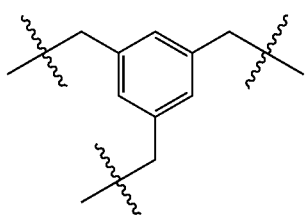
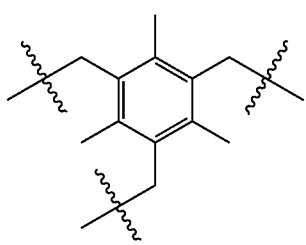
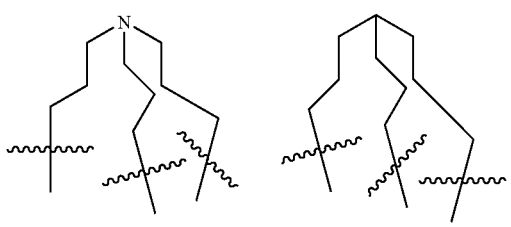
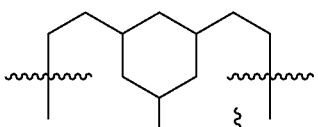
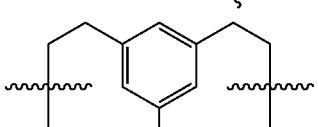
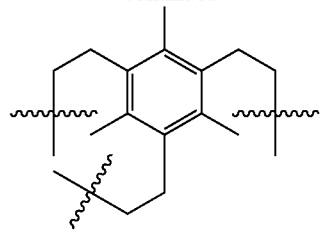
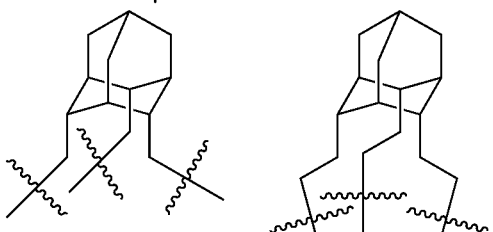
and
R3, R4, and R5 are independently selected from:
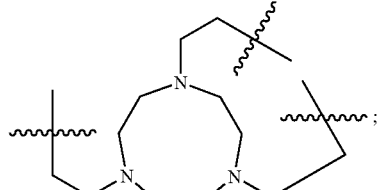
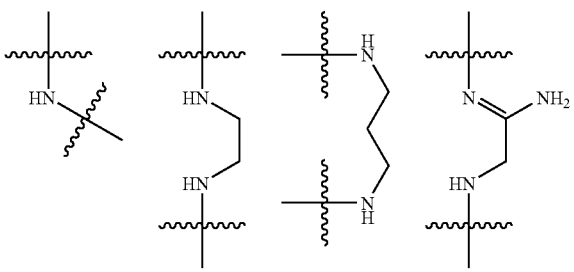
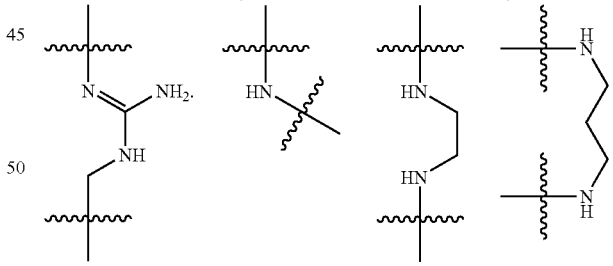
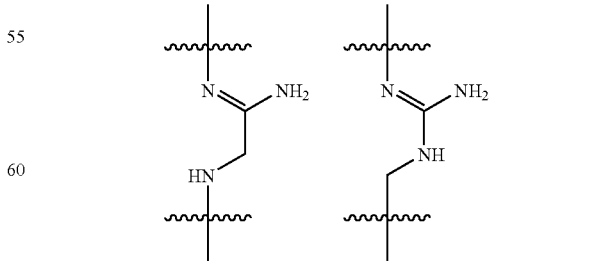
More preferably in this aspect of the invention, the Cryptand is selected from:

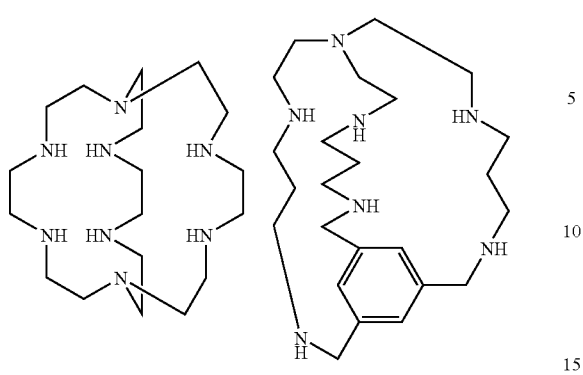

Preferred compounds of formula (III) used to prepare the compounds of formula (I) include:

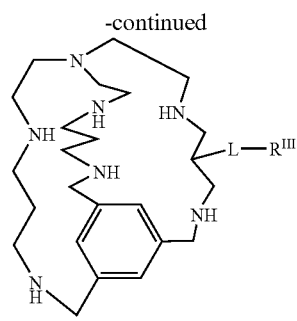

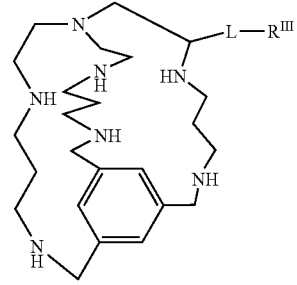

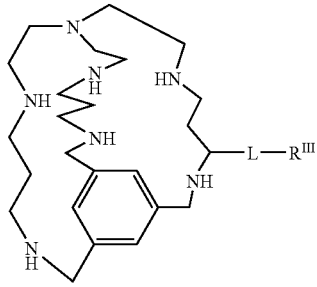

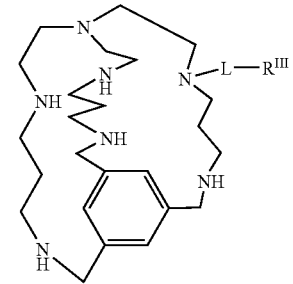

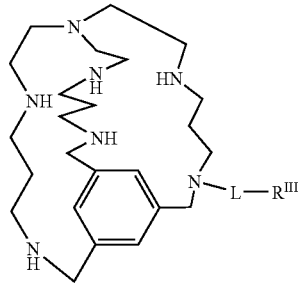

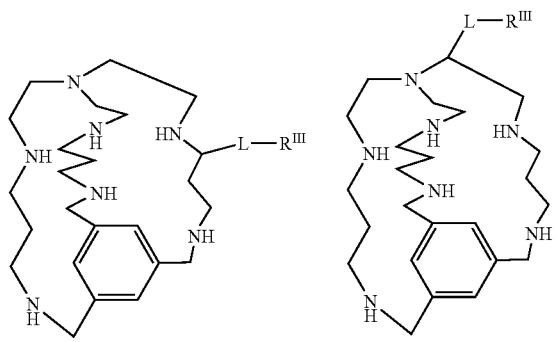

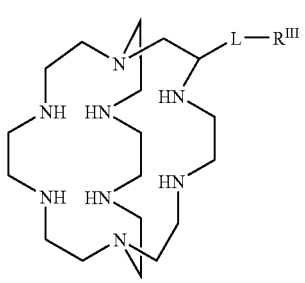

wherein L is a Linker' as defined above, and $R^{III}$ is a reactive group as defined above, and is preferably selected from amine, carboxylic acid, activated carboxylic ester, isocyanate, isothiocyanate, thiol, maleimide, or α-halocarbonyl.

More preferred compounds of formula (III) used to prepare the compounds of formula (I) include:

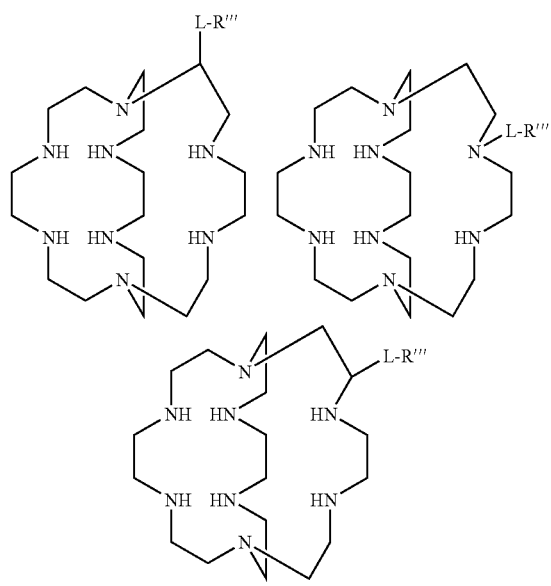

wherein L is a Linker' as defined above, and R$^{III}$ is a reactive group as defined above, and is preferably selected from amine, carboxylic acid, activated carboxylic ester, isocyanate, isothiocyanate, thiol, maleimide, or α-halocarbonyl.

According to a further aspect of the invention there is provided an apparatus for preparation of an [$^{18}$F]fluoride solution by a method as described above. Therefore, there is provided an apparatus for preparation of an [$^{18}$F]fluoride solution which comprises:
(i) a vessel containing a solid-support bound Cryptand of formula (I) as defined above;
(ii) means for contacting a solution of [$^{18}$F]fluoride in water with said solid-support bound Cryptand of formula (I) so as to form a Cryptand-[$^{18}$F]fluoride complex of formula (II) as defined above;
(iii) means for removal of excess water from the Cryptand-[$^{18}$F]fluoride complex of formula (II);
(iv) means for washing the Cryptand-[$^{18}$F]fluoride complex of formula (II) with a solution of base, suitably a base having a pKa of at least 9, so as to release the [$^{18}$F]fluoride into solution.

In a further embodiment, the apparatus forms part of, or is in fluid communication with, an automated radiosynthesis apparatus such that following preparation of the [$^{18}$F]fluoride solution by a method of the invention, the [$^{18}$F]fluoride solution is used in an [$^{18}$F]fluoridation reaction. In one embodiment, the apparatus is a microfabricated device—either dedicated to preparation of an [$^{18}$F]fluoride solution or further incorporating means to effect a radiofluoridation reaction.

In use of the apparatus, the solid-support bound Cryptand of formula (I), would be contacted with a solution of [$^{18}$F]fluoride in water using methods described above to form the corresponding compound of formula (II) and then washed with a solution of base, suitably a base having a pKa of at least 9 so as to release the [$^{18}$F]fluoride into solution.

Reviews of methods for construction of microfabricated devices and their application inter alia in synthetic chemistry, may be found in DeWitt, (1999) "Microreactors for Chemical Synthesis", Current Opinion in Chemical Biology, 3:350-6; Haswell, Middleton et al (2001) "The Application of Microreactors to Synthetic Chemistry", Chemical Communications: 391-8; Haswell and Skelton (2000) "Chemical and Biochemical Microreactors", Trends in Analytical Chemistry 19(6), 389-395; and Jensen (2001) "Microreaction Engineering—Is Small Better?" Chemical Engineering Science, 56:293-303.

Suitable microfabricated devices for performing the methods of the invention have a contained network of microchannels or capillaries having an internal diameter of typically 10-300 μm, more typically 50-300 μm. The network of microchannels or capillaries may be etched or otherwise machined on the surface of a substrate, suitably made of glass or silicon. Alternatively, the microchannels may be created using polymers (for example PEEK plastic, cycloolefin copolymer, polydimethylsiloxane, SU8 (an epoxy based photoresist), epoxy resin, or polymethylmethacrylate) which may be poured over a master (usually glass), allowed to cure and then peeled off, or are fabricated by injection moulding, hot embossing, casting, lithography, or machining.

The microchannels or capillaries may be sealed through bonding of a cover plate, suitably made from a metal (for example, gold or silver) or, more commonly, glass, creating a contained network capable of manipulating picoliter volumes of liquid or gas. The sealing method used depends on the materials selected and may be selected from thermal bonding (for glass chips), anodic bonding (for silicon chips), and for polymer chips the sealing method may be selected from clamping, gluing, application of heat and pressure, and natural adhesion. Flow capacity could be increased further, for example, by stacking multiple devices. These devices are designed to be used either with micro syringe pumps (available from Kloehen Limited, Las Vegas, USA) or under electroosmotic flow using fused silica capillaries for interfacing with reagents and analytical systems (such as ultraviolet (UV), capillary electrophoresis (CE), capillary electrochromatography (CEC), electrochemical, refractive index, and radioactivity detectors).

Where the vessel is a microchannel in a microfabricated device, it may be coated with a solid-support bound Cryptand of formula (I) by conventional methods, for example analogous to those described in WO2005/061110. Surface modification of poluethylene is reviewed in the book Advances in Polymer Science (Springer Berlin/Heidelberg ISSN 0065-3195 (Print) 1436-5030 (Online) Volume 169 DOI 10.1007/b13502 Copyright 2004 ISBN 978-3-540-40769-0 DOI 10.1007/b13524 Pages 231-294). Many of the techniques described will apply to other plastic materials. Where the microfabricated device is constructed from poly(methyl metacrylate) (PMMA), the surface of the PMMA may be amine functionalized as described in Anal. Chem., 72 (21), 5331-5337, 2000. PMMA devices may also be functionalized as sulfhyril group as described in United States patent application 20050101006. Photografting allows the introduction of surface functional groups to a range of polymeric materials such as polycarbonates, PMMA, polydimethylsiloxane and polyolefins as described in Rohr, T., Ogletree, F. D., Svec, F., Fréchet, J. M., "Surface Functionalization of Thermoplastic Polymers for the Fabrication of Microfluidic Devices by Photoinitiated Grafting," Adv. Funct. Mater. 2003, 13, 264-70. In addition, the reactive surface area may be increased by using chemically grafted three dimensional monoliths which can be included in a microfabricated device as described in Rohr, T., Ogletree, F. D., Svec, F., Fréchet, J. M., "Photografting and the Control of Surface Chemistry in Three-Dimensional Porous Polymer Monoliths," Macromolecules 2003, 36, 1677-84 and Stachowiak, T. B., Rohr, T., Hilder, E. F., Peterson, D. S., Yi, M., Svec, F., Fréchet, J. M., "Fabrication of Porous Polymer Monoliths Covalently Attached to the Walls of Channels in Plastic Microdevices," Electrophoresis 2003, 24, 3689-93. Furthermore, the microfabricated device may also cantain dual functionality where for example, in addition to the covalently bound cryptand, there may be an additional reagent e.g. solid supported substrate or chemical scavenger. Dual function devices are described in Peterson, D. S., Rohr, T., Svec, F., Fréchet, J. M., "Dual-Function Microanalytical Device by In Situ Photolithographic Grafting of Porous Polymer Monolith: Integrating Solid-Phase Extraction and Enzymatic Digestion for Peptide Mass Mapping," Anal. Chem. 2003, 75, 5328-35.

The invention is illustrated by way of the following examples, in which these abbreviations are used:
Et$_3$N: triethylamine
R.T.: room temperature
MeOH: methanol
(t) BOC: (tertiary) butoxycarbonyl
L: liter
mL: milliliter
hr(s): hour(s)
THF: tetrahydrofuran
HPLC: high performance liquid chromatography
DCM: dichloromethane
LCMS: liquid chromatography mass spectrometry
NMR: nuclear magnetic resonance
TFA: trifluoroacetic acid
MBq: Mega Bequerel
RCP: radiochemical purity

EXAMPLES

Example 1

Synthesis of compound 4

Example 1(i)

Synthesis of Compound 1

A 1 L 3-neck round-bottom flask equipped with a mechanical stirrer was charged with 16.7 mL of 98% tripropylamine and 0.33 L of 99% isopropanol, and cooled to −78° C. in a dry ice-isopropanol bath. To this mixture, solutions of 15.0 g 40% aqueous glyoxal (0.103 mole), diluted to 83 mL with isopropanol, and 10.0 g (0.0.683 moles) of 96% tris-(2-aminoethyl) amine(tren), diluted to 83 mL, were simultaneously added over a period of 2 hrs with vigorous stirring. (Initial concentration of glyoxal=1.24 M; Initial concentration of tren=0.82 M). Then the reaction mixture was allowed to warm up overnight and briefly warmed up to 60° C. to ensure that the formation of compound 2 was complete. It was cooled to room temperature while nitrogen gas was blown over its surface. The solvent was removed under vacuum and chloroform (250 mL) was added. The resulting slurry was filtered through sand and concentrated under vacuum to give an orange solid (5.2 g, 43%).

Example 1(ii)

Synthesis of Compound 2

Compound 1 (4 g, 11.2 mmol) was dissolved in methanol ((150 mL) and was cooled in an ice/water bath. Sodium borohydride (8 g, 208 mmol) was added portion wise over 30 minutes. The mixture was left to rise to room temperature with stiffing over 16 hours. The solution was concentrated to dryness under vacuum to give an off white solid. The solid was dissolved in water (100 mL) and was heated to 60° C. for half an hour during which time an oily material formed in the

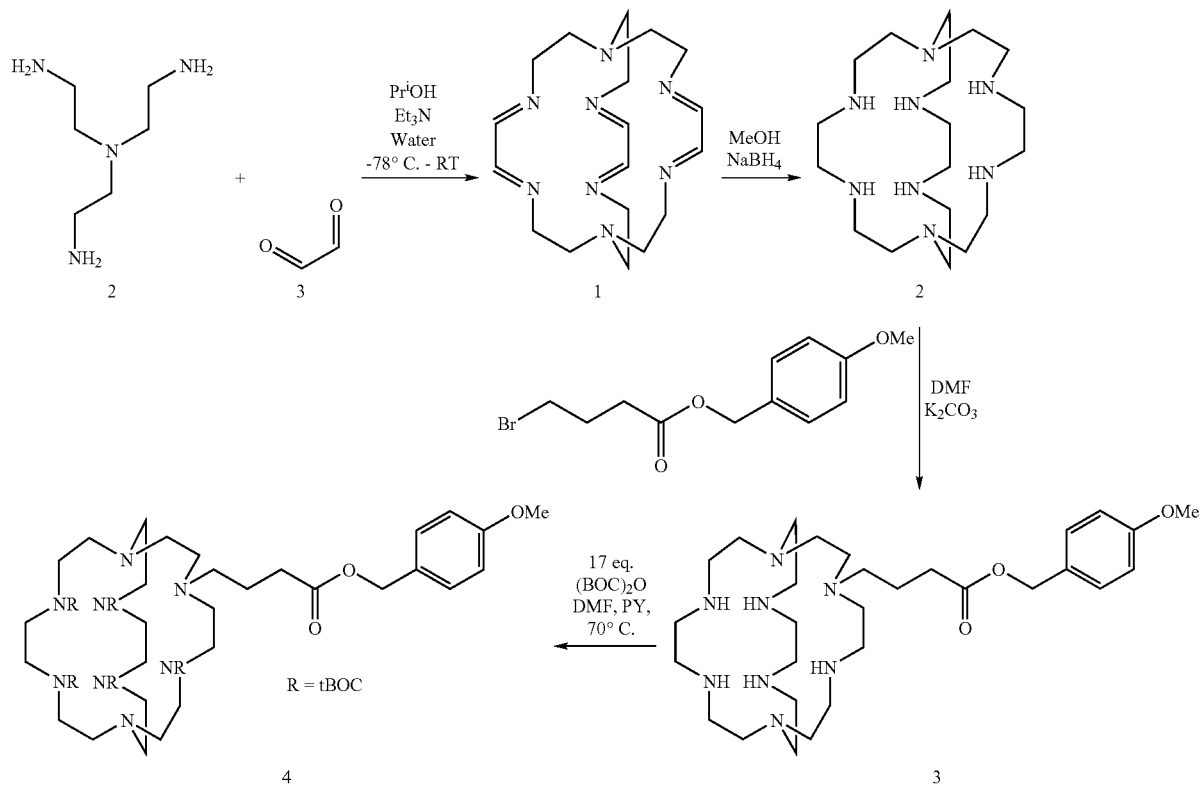

mixture. THF (100 mL) was added and the organic layer was separated. The aqueous layer was extracted again with THF (100 mL). The combined extracts were filtered through a phase separator cartridge and were concentrated to dryness under vacuum. The oily solids were re-dissolved in THF (20 mL) and water (15 mL) was added. The solution was concentrated slowly until a white solid crystallized which was collected by filtration, washed with ice cold water and dried under high vacuum (1.6 g, 38%).

Example 1(iii)

Synthesis of Compound 3

Compound 2 (0.1 g, 0.270 mmol) was dissolved in dry DMF (5 mL) and potassium carbonate added (1.1 eq. 0.297 mmol, 0.041 g). The alkyl bromide (1.1 eq. 0.297 mmol, 81.7 mg) was added portion wise following the reaction by HPLC-mass spectrometry by taking approximately 0.1 mL volume from the reaction and diluting with 1:1 0.1% formic acid in water:acetonitrile (10 mL). The reaction was stirred at room temperature for 16 hours. A further 0.25 equivalents of the alkyl bromide was added and the reaction stirred for a further 16 hours. The reaction mixture was concentrated to dryness under vacuum. This was used in the next step without further purification.

Example 1(iv)

Synthesis of Compound 4

Crude compound 3 was dissolved in dry DMF (20 mL) and pyridine (2 mL) was added followed by di-tert-butylcarbonate (1 g, 4.58 mmol, 17 eq.). The mixture was heated at 70° C. under nitrogen for 16 hours. The crude product was analysed by thin layer chromatography (silica gel plates eluting with 10% methanol/DCM) and by LCMS. Thin layer chromatography showed two major spots having Rf values of 0.2 and 0.5 and some minor spots. The mixture was purified by flash column chromatography on silca gel eluting with 100% petrol 40-60 to 100% ethyl acetate. The second major peak was shown to be the desired penta-BOC product by NMR and LCMS (50 mg).

Example 2

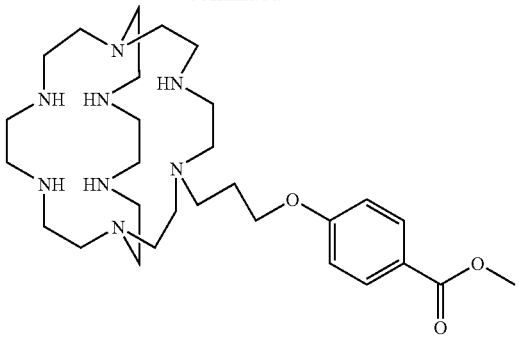

5

Example 2(i)

Synthesis of Compound 5

Compound 2 (0.1 g, 0.270 mmol) was dissolved in dry DMF (2 mL) and a solution of the alkyl bromide (1.1 eq. 0.297 mmol, 81.07 mg) in dry DMF (1 mL) was added over 5 minutes. The solution was stirred at room temperature for 16 hours. The DMF was removed under reduced pressure and white solids dissolved in an minimum volume of water/methanol (1:1). Preparative HPLC (Phenomenex luna C18(2) 150×21.2, acetonitrile/water 5% to 70% over 10 minutes) gave a major peak having $t_r$ of 8-8.5 minutes which was freeze dried giving an white solid (15 mg). NMR and LCMS confirmed the structure.

Example 2(ii)

Fluoride Binding Studies with [$^{18}$F]-Fluoride

Compound 5 (1 mg) in water (0.1 mL) acidified to pH 1 with 1N HCl and an aqueous solution of potassium fluoride (0.1-1 eq) was added at RT. The solutions were analysed by reversed phase HPLC (1% TFA/water, 1% TFA MeCN gradient on Luna C5 150×4.6 mm, detecting at 254 nm).

Example 2(iii)

Fluoride Radiolabelling of Compound 5 with [$^{18}$F]-Fluoride

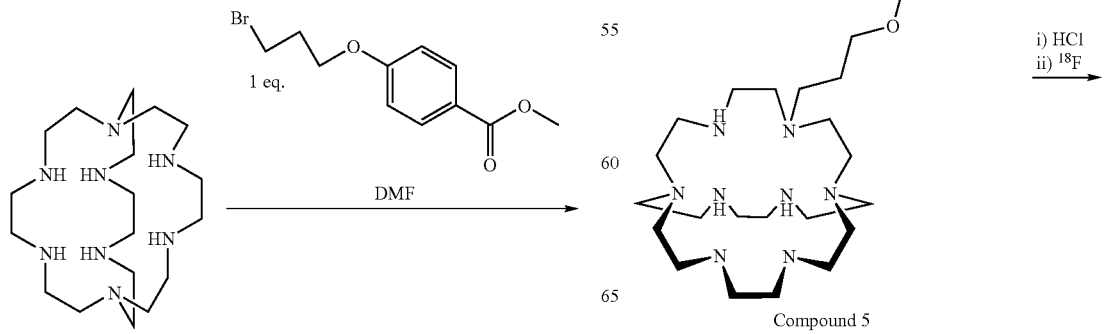

Compound 5

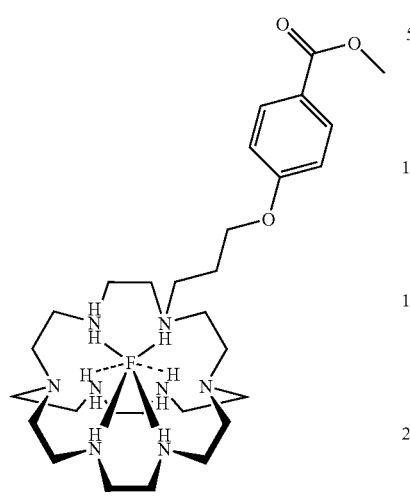

1M HCl (4.5 μL, 4.5 μmol) was added to compound 5 (0.1 mg, 180 nmol) in 50:50 methanol/water (0.2 mL). This acidified solution was added directly to a glass vial containing [$^{18}$F]fluoride (98 MBq) in target water (0.05 mL) and left at room temperature for 20 minutes. The reaction was analyzed by reverse phase H PLC (solvent A=0.1% TFA in water; Solvent B=0.1% TFA in MeCN, Luna C5 150×4.6 mm, detecting at 254 nm; Gradient: 0 to 3 minutes (2% B), 3-10 minutes (2 to 70% B), 10 to 13 minutes (70% B); 13 to 16 minutes (70 to 2% B), 16 to 21 minutes (2% B); flow rate 1 mL/minute. [$^{18}$F]-5 has a retention time of 10.1 minutes. [$^{18}$F]-5 was purified using the same HPLC method with a decay corrected isolated yield of 64%. Purified [$^{18}$F]-5 is stable (>95% RCP) in an acidic solution (pH<3).

Increasing the pH [$^{18}$F]-5 solution to pH 7 results in the removal of more than 70% of the [$^{18}$F]-fluoride from the cryptand as measured by HPLC peak instensity.

HPLC Conditions:

| | |
|---|---|
| 0-3 mins | 2% (B) |
| 3-10 mins | 2-70% (B) |
| 10-13 mins | 70% (B) |
| 13-16 mins | 70-2% (B) |
| 16-21 mins | 2% (B) |
| Column | Luna C5 150 × 4.6 mm |
| Eluent | Solvent A: 0.1% TFA in water; Solvent B: 0.1% TFA in acetonitrile |
| Pump speed | 1 mL/min, |
| Wavelength | 254 nm |

Example 3

Synthesis of a Resin Bead-Bound Solid Supported Cryptand

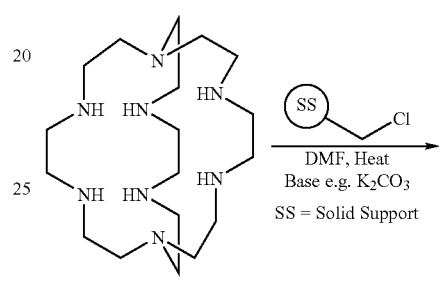

Compound 2 and a base e.g. potassium carbonate are dissolved in dry DMF (2 mL) and is added to a suspension of (chloromethyl)polystyrene resin (e.g. Merrifield's peptide resin available from Sigma-Aldrich) in dry DMF (1 mL) was added over 5 minutes. The mixture is agitated at room temperature or elevated temperature until the free cryptand starting material is consumed (determined by LCMS). The DMF was removed by filtration and the resin washed a number of times with one or more organic solvents e.g. methanol, dichloromethane or dimethylformamide. The final resin is characterized by elemental analysis.

Example 2

Synthesis of a Resin Bead-Bound Solid Supported Cryptand

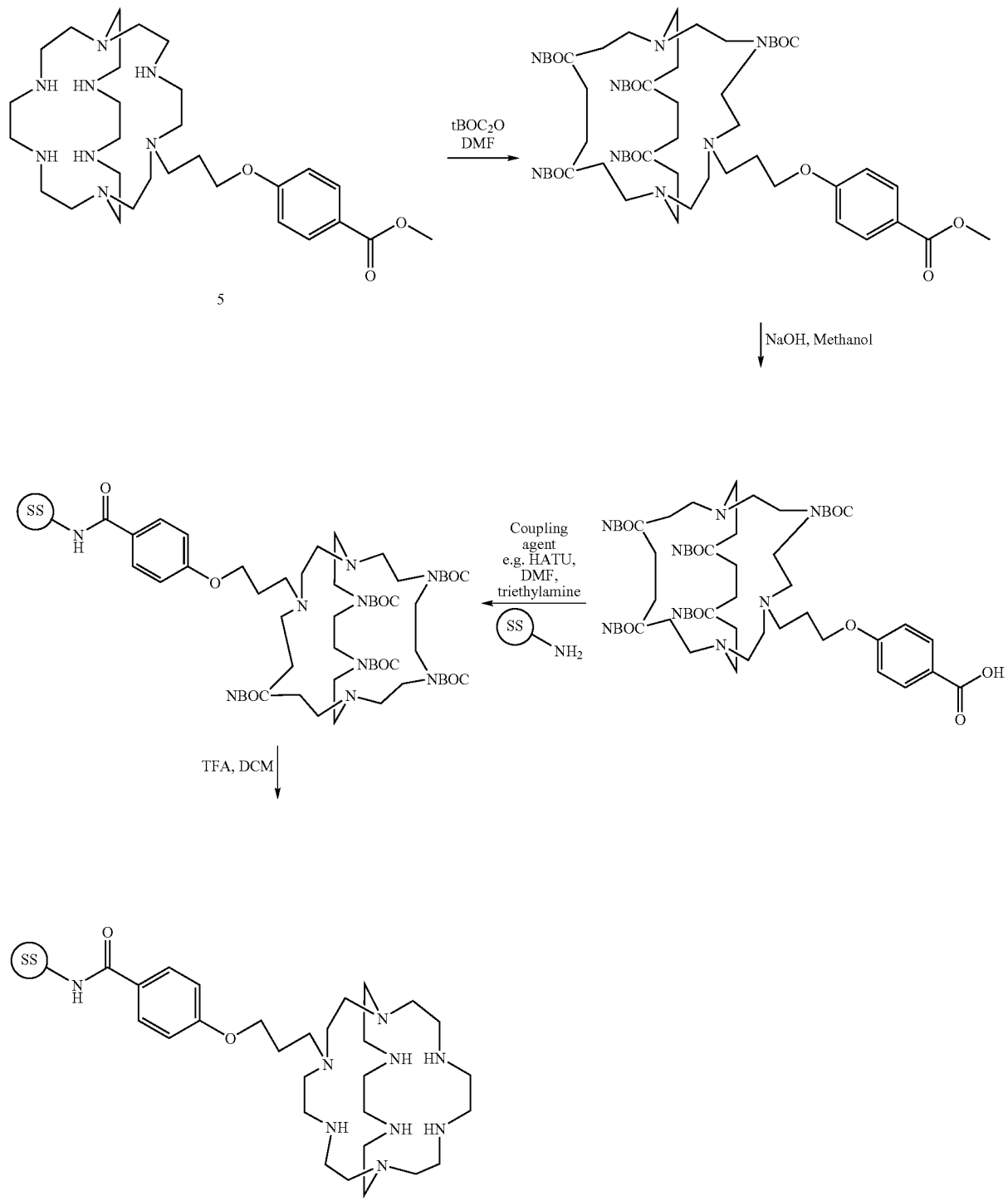

Compound 5 is treated with an excess of tBOC anhydride to give the corresponding penta-BOC protected species. Saponification of the methyl ester to give the free acid, followed by amide bond formation with an amino-functionalized resin (e.g. (aminomethyl)polystyrene resin available from Sigma-Aldrich) using a coupling reagent (e.g. HATU) gives the solid-supported BOC protected cryptand. Finally, BOC de-protection using trifluofoacetic acid gives the desired solid-supported cryptand. This is characterized by NMR and elemental analysis.

What is claimed is:

1. A method for preparing a concentrated [$^{18}$F]fluoride solution in a form suitable for radiofluorination which comprises:
  (i) contacting a solution of [$^{18}$F]fluoride in water with a solid-support covalently-bound Cryptand of formula (I):

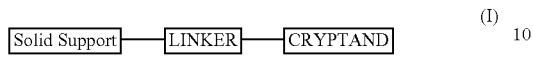
(I)

at a pH of less than 5 so as to form a Cryptand-[$^{18}$F]fluoride complex of formula (II):

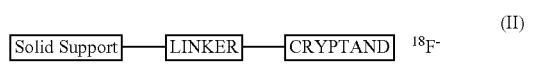
(II)

(ii) removal of excess water from the Cryptand-[$^{18}$F]fluoride complex of formula (II);
  (iii) washing the Cryptand-[$^{18}$F]fluoride complex of formula (II) with a solution of base so as to release the [$^{18}$F]fluoride into solution, characterized in that said solution has a volume of 400 μl or less, and is in either:
    (a) a dry organic solvent having less than 1000 ppm water; or
    (b) an organic solvent having a water level tolerated in radiofluorination reactions, i.e. containing 1000 to 50,000 ppm water;
  wherein said cryptand has 3 to 12 donor atoms which are all N donor atoms;
  and wherein the [$^{18}$F]fluoride solution obtained in step (iii) is in a form suitable for radiofluorination without any further water removal step.

2. A method according to claim 1 wherein the Cryptand is of formula (C):

(C)

wherein:
R1 and R2 are independently selected from

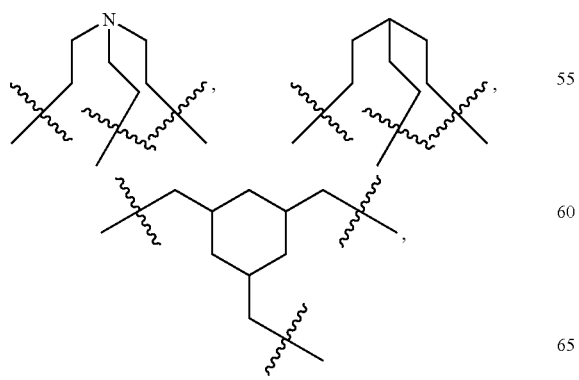

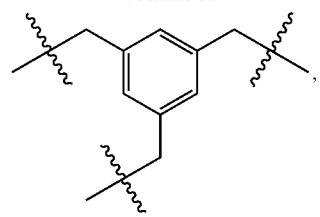

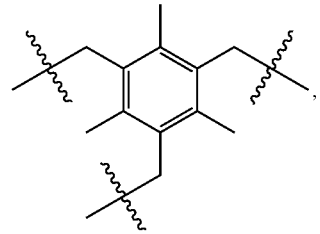

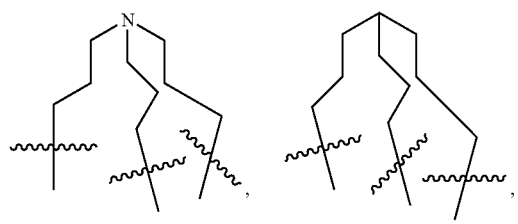

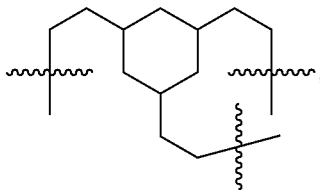

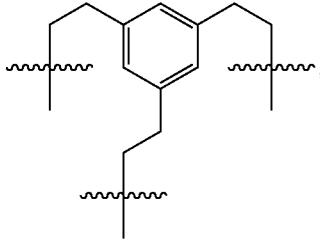

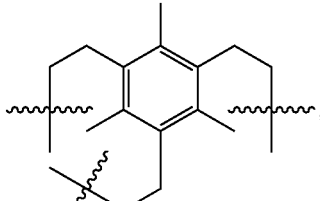

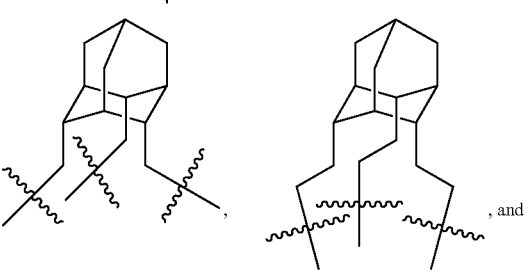

-continued

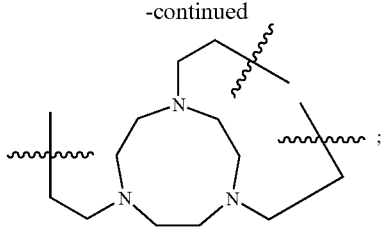

and
R3, R4, and R5 are independently selected from:

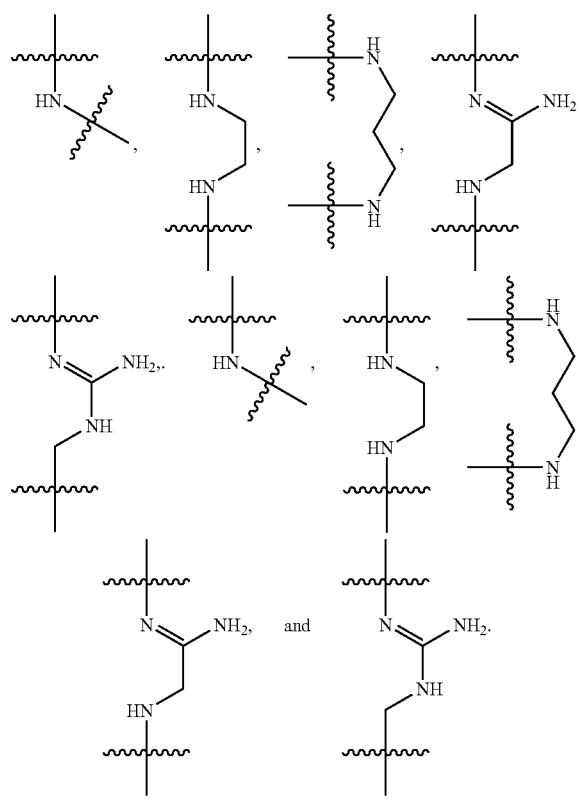

3. A method according to claim 1 wherein the Cryptand is selected from

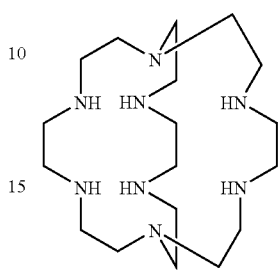 and 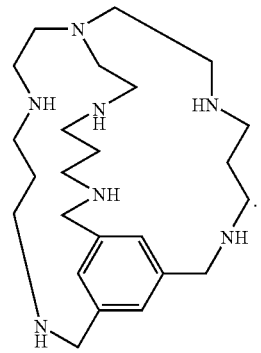.

4. A method according to claim 1 wherein said base of step (iii) is selected from: a potassium salt optionally in the presence of a phase transfer catalyst; a tetraalkylammonium salt; a phosphonium salt; a cesium salt; and an imidazolium salt; and wherein said organic solvent is acetonitrile, dimethylformamide, dimethylsulfoxide, tetrahydrofuran, dioxan, 1,2-dimethoxyethane, sulfolane or N-methylpyrrolidinone or a mixture of any thereof, or an organic solvent further containing water.

5. A method according to claim 1 wherein step (iii) is performed using a solution of potassium carbonate and Kryptofix in acetonitrile optionally containing water.

6. A method according to claim 1 further comprising reaction of the resultant [$^{18}$F]fluoride solution of step (iii) with a Vector.

* * * * *